United States Patent

Terao et al.

[11] Patent Number: 6,133,278
[45] Date of Patent: Oct. 17, 2000

[54] USE OF QUINONE AND HYDROQUINONE DERIVATIVES FOR THE TREATMENT OF CACHEXIA

[75] Inventors: Shinji Terao, Toyonaka, Japan; Michael John Tisdale, Claverdon, United Kingdom

[73] Assignee: Takeda Chemical Industries, Ltd., Osaka, Japan

[21] Appl. No.: 08/528,152

[22] PCT Filed: Aug. 10, 1995

[86] PCT No.: PCT/JP95/01594

§ 371 Date: Sep. 14, 1995

§ 102(e) Date: Sep. 14, 1995

[87] PCT Pub. No.: WO96/04909

PCT Pub. Date: Feb. 22, 1996

[30] Foreign Application Priority Data

Aug. 12, 1994 [JP] Japan .................................. 6-190732

[51] Int. Cl.⁷ ..................... A61K 31/435; A61K 31/425; A61K 31/42; A61K 31/415
[52] U.S. Cl. ................ 514/277; 514/372; 514/374; 514/401
[58] Field of Search ................... 514/277, 372, 514/374, 401

[56] References Cited

U.S. PATENT DOCUMENTS 4,851,413  7/1989  Terao et al. ............................ 514/277

FOREIGN PATENT DOCUMENTS 0 234 729  12/1991  European Pat. Off. .
WO92/10190  6/1992  WIPO .
WO92/10498  6/1992  WIPO .

OTHER PUBLICATIONS

Ohkawa et al., *The Journal of Medicinal Chemistry*, vol. 34, No. 1, 1991, pp. 267–276.
Willette et al., *Pharmacology Communications*, vol. 1, No. 4, 1992, pp. 329–335.
Dinarello et al., *Annals of the New York Academy of Sciences*, vol. 587, 1990, pp. 332–338.
Cryan et al., *Prostaglandins Leukotrienes and Essential Fatty Acids* (1990) 39 (4) pp. 311–317.

Primary Examiner—Jerome D. Goldberg
Attorney, Agent, or Firm—Wenderoth, Lind & Ponack, LLP.

[57] ABSTRACT

A pharmaceutical composition for treating cachexia which containing a compound (I)

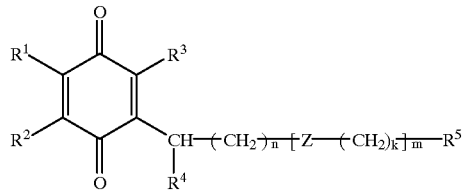

wherein $R^1$, $R^2$ is H, alkyl, alkoxy, may form —CH=CH—CH=CH—; $R^3$ is H, alkyl; $R^4$ is N-containing heterocyclic; $R^5$ is H, alkyl, hydroxyalkyl, carboxyl; Z is

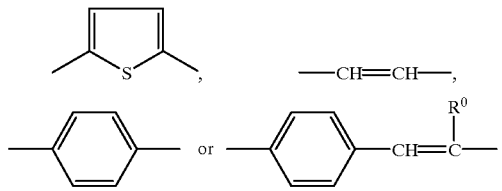

($R^0$ is H, alkyl); n is 0–12; m is 0–3; k is 0–7, or a salt thereof.

15 Claims, 2 Drawing Sheets

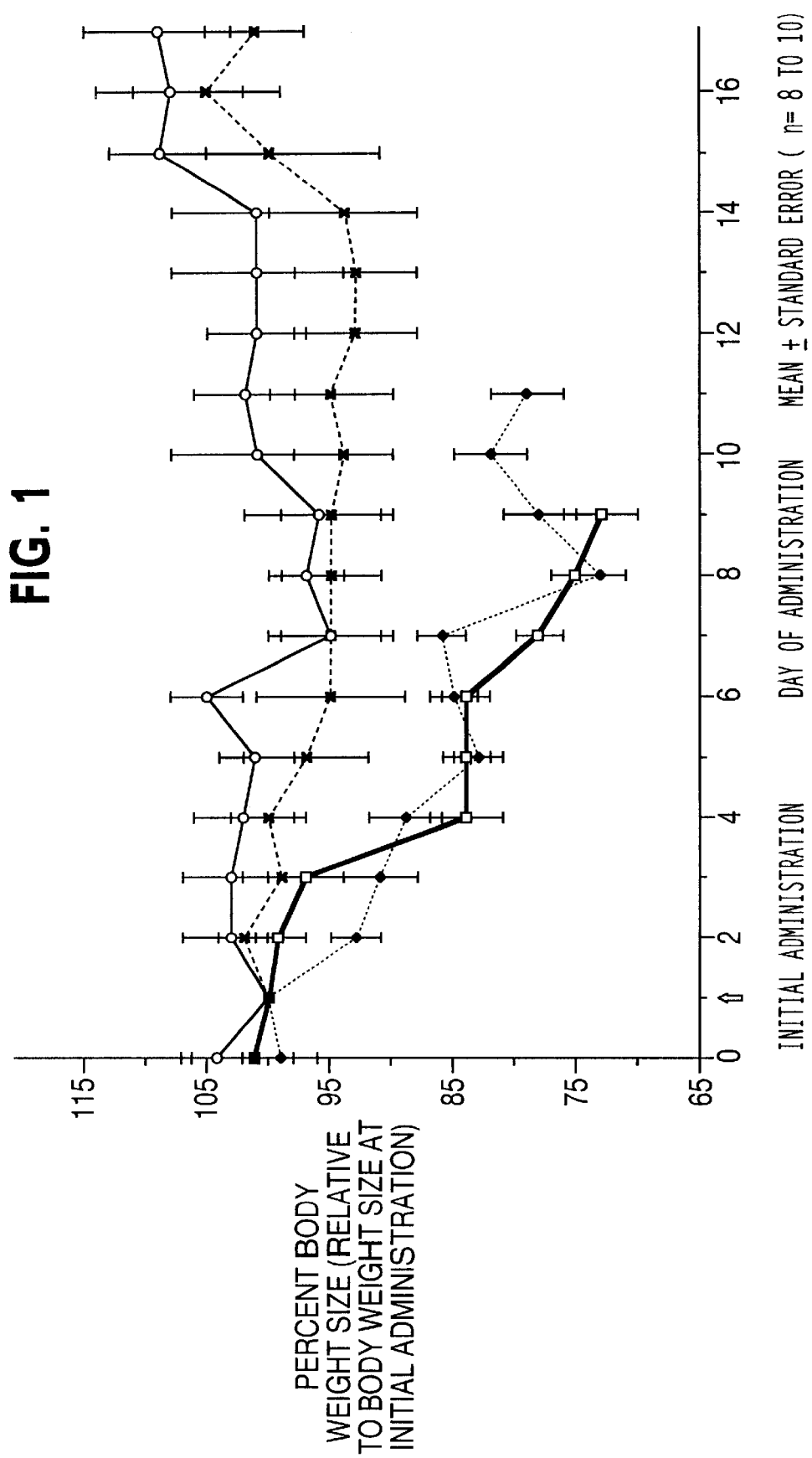

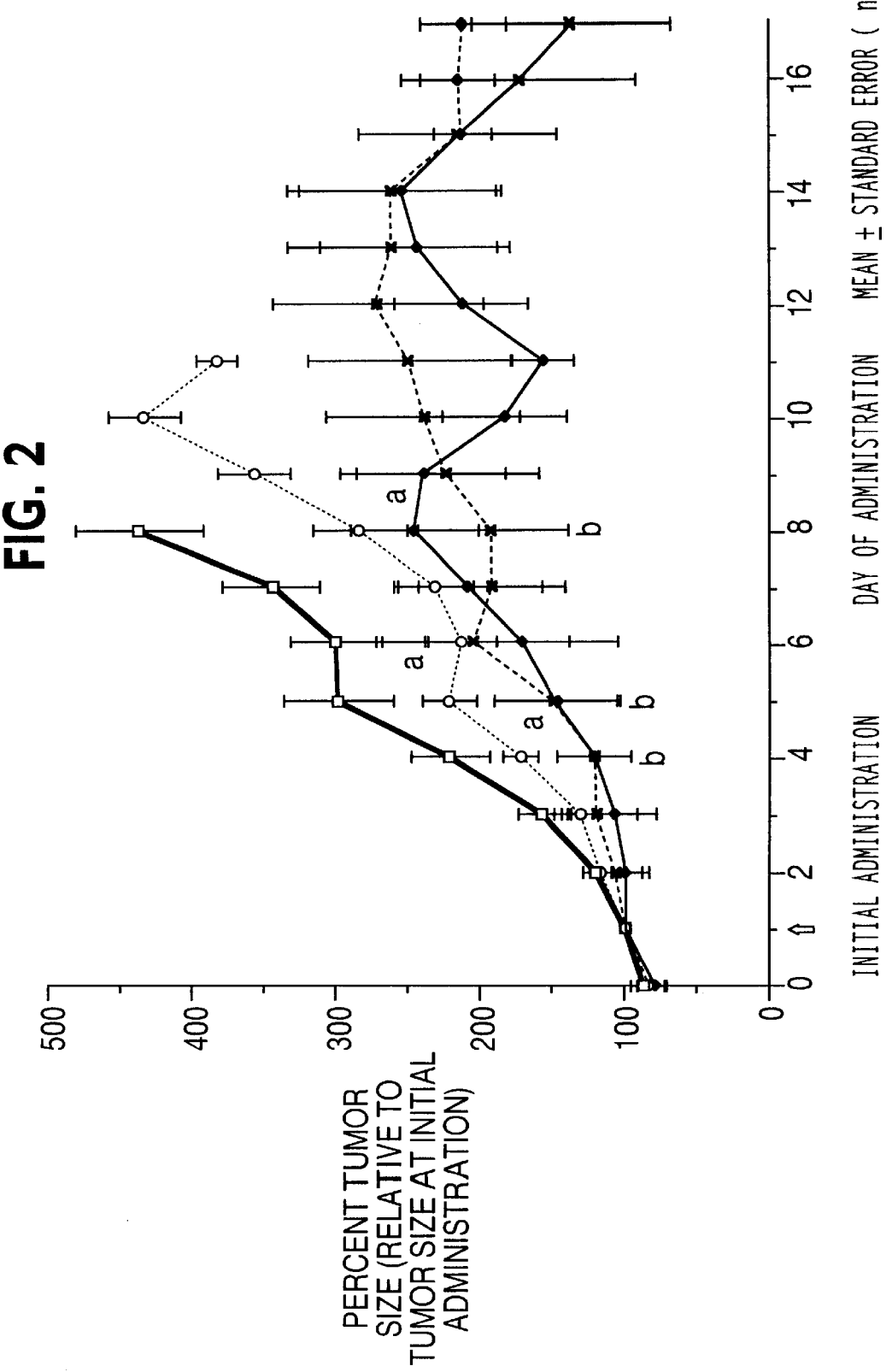

USE OF QUINONE AND HYDROQUINONE DERIVATIVES FOR THE TREATMENT OF CACHEXIA

This application is a §371 application of PCT/JP95/01594, filed Aug. 10, 1995, which is a continuation of Japan 190732, filed Aug. 12, 1994.

DESCRIPTION

This invention relates to a pharmaceutical agent for the prevention and therapy of cachexia associated with chronic diseases such as malignant tumor, tuberculosis, diabetes, hemodyscrasia and endocrinopathy, among other diseases, which comprises a quinone compound as an active ingredient.

TECHNICAL FIELD

Cachexia involves progressive loss of body weight, anemia, edema and anorexia as cardinal symptoms, which is associated with malignant tumor, tuberculosis, diabetes, homodyscrasia, endocrinopathy, AIDS and so on "J. Parenteral and Enteral Nutrition, 12, 286–298, 1988" and "American Journal of Medicine, 85, 289–291, 1988".

Against cachexia, parenteral or enteral nutrition and endocrine therapy, for instance, have been attempted so far but no satisfactory therapeutic modality has been established as yet. Particularly where cachexia is caused by a malignant tumor, progression of cachexia diminishes the tolerance of patients for anticancer chemotherapy so that the treatment encounters a serious setback. On the other hand, palliative nutritional support for cachexia rather may exacerbate the malignant tumor to reduce the survival period of the patient. While cachexia is frequently induced by malignant tumors, administration of antitumor drugs may bring about antitumoral effects but it is the rule rather than exception that side effects of antitumor medication are superimposed to arrest a remission of cachexia.

There exists, under the circumstances, a need for a therapeutic drug that would ameliorate or inhibit progression of cachectic symptoms such as loss of body weight.

The present inventors previously constructed a cachexia model in mice by transplanting the colorectal cancer MAC16 of a mouse which had developed cachexia associated with the malignant tumor and showing clinical manifestations resembling those of a patient with cachexia in the abnormalities of lipid and protein metabolisms "British Journal of Cancer, 63, 337–342, 1991". In this model, chemotherapeutic agents in use clinically do not ameliorate cachexia and many of them do not show an antitumoral effect, either. Therefore, this model was found to be suitable for the evaluation of drugs for palliation of cachexia "Journal of National Cancer Institute, 81, 988–994, 1989". Meanwhile, for the purpose of solving the above problems, the inventors proceeded with an exploration for compounds antagonizing various symptoms of cachexia, such as loss of body weight, and as the result of intensive research, discovered that a certain class of quinone compounds has such activity.

BACKGROUND ART

EP-234729 describes that quinone compounds, exhibit two or more actions out of improvement of metabolism of higher unsaturated fatty acids (linoleic acid, γ-linolenic acid, α-linolenic acid, arachidonic acid, di-homo-γ-linolenic acid, eicosapentaenoic acid), particularly suppression of peroxy fatty acid production (antioxidant action) or suppression of production of 5-lipoxygenase metabolites (e.g., leukotrienes, 5-hydroxyeicosatetraenoic acid, 5-peroxyeicosatetraenoic acid, lipoxins), thromboxane $A_2$ synthetase inhibition, thromboxane $A_2$ receptor antagonist, and active oxygen elimination, and that they are pharmaceutically useful as antithrombotic agents, antivasospasmodic agents, anti-asthmatic agents, anti-allergic agents, antipsoriatic agents, cardio-cerebro vascular circulation improving agents, nephritis remedies, active oxygen eliminators, anticancer agents and arachidonic acid cascade substance regulation improving agents. However, it does not mention cachexia.

DISCLOSURE OF INVENTION

With the aim of solving the above problems, the present inventors investigated in search of compounds that suppress various cachectic symptoms such as body weight loss, and found that quinone derivatives exhibit these effects.

The present invention relates to a prophylactic/therapeutic agent for a cachexia containing, as an active ingredient, a quinone derivative represented by the formula (I):

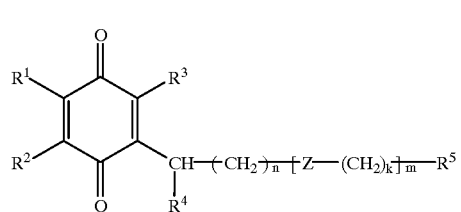

(I)

wherein $R^1$ and $R^2$ independently represent a hydrogen atom, an alkyl group, an alkenyl group or an alkoxy group, or may bind together to form —CH=CH—CH=CH—; $R^3$ represents a hydrogen atom, an alkyl group, an alkenyl group; $R^4$ represents an optionally substituted nitorgen-containing heterocyclic group; $R^5$ represents a hydrogen atom, an alkyl group, an optionally substituted hydroxyalkyl group or an optionally esterified or amidated carboxyl group; Z represents a group represented by

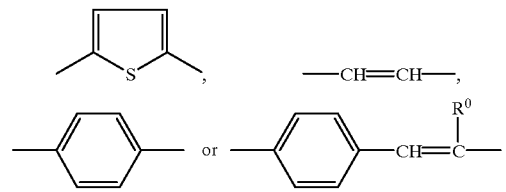

($R^0$ represents a hydrogen atom or an alkyl group); n represents an integer from 0 to 12, m represents an integer from 0 to 3, k represents an integer from 0 to 7; Z and k are arbitrarily variable within the repeat unit in [ ], a hydroquinone derivative thereof or a pharmaceutically acceptable salt thereof.

With respect to the above formula (I), the term "alkyl group" represented by $R^0$, $R^1$, $R^2$, $R^3$ and $R^5$ stands for a lower alkyl group having one to six carbon atom(s) such as a methyl, ethyl, propyl, isopropyl butyl, isobutyl, sec-butyl, tert-butyl, and so on. Preferable example of the "alkyl group" is a methyl group.

With respect to the above formula (I), the term "alkenyl group" represented by $R^1$, $R^2$ and $R^3$ stands for a lower alkenyl group having two to six carbon atoms such as a vinyl, allyl, isopropenyl, butenyl, isobutenyl, sec-butenyl, and so on. Preferable example of the "alkenyl group" is a vinyl group.

With respect to the above formula (I), the term "alkoxy group" represented by $R^1$ and $R^2$ stands for a lower alkoxy group having one to six carbon atom(s) such as a methoxy, ethoxy, propoxy, isopropoxy, butoxy, isobutoxy, sec-butoxy, tert-butoxy, and so on. Preferable example of the "alkoxy group" is a methoxy group.

With respect to the above formula (I), the term "nitrogen-containing heterocyclic group" represented by $R^4$ stands for a 5- or 6-membered heterocyclic group which contains (i) one nitrogen atom as a ring-forming atom or (ii) one nitrogen atom and one or two hetero atom(s) selected from a nitrogen, oxygen and sulfur atom as ring-forming atom(s) such as a pyridyl group (e.g. 2-pyridyl, 3-pyridyl, 4-pyridyl), a thiazolyl group (e.g. 2-thiazoyl, 4-thiazolyl, 5-thiazolyl), an imidazolyl group (e.g. 1-imidazolyl, 2-imidazolyl, 4-imidazolyl, 5-imidazolyl) and a quinolyl group (e.g. 2-quinolyl, 3-quinolyl, 4-quinolyl). The preferred are a 5- or 6-membered heterocyclic group containing at least one nitrogen atom as a ring-forming atom such as a pyridyl (especially 3-pyridyl), a thiazolyl (especially 5-thiazolyl) and an imidazolyl (especially 1-imidazolyl) and the most preferred is a pyridyl (especially 3-pyridyl). These nitrogen-containing heterocyclic groups may have one to three substituent(s) at any positions on the ring thereof. Such substituents include a $C_{1-6}$ alkyl group (e.g. methyl, ethyl), a $C_{1-6}$ alkoxy group (e.g. methoxy, ethoxy), a $C_{1-6}$ alkylthio group (e.g. methylthio, ethylthio), an amino group, mono- or di-$C_{1-6}$ alkylamino group (e.g. methylamino, dimethylamino), a halogen (e.g. fluorine, chlorine), a nitro group, a mercapto group, a sulfo group, a cyano group, a hydroxyl group, a carboxyl group, a $C_{1-6}$ alkoxy-carbonyl group (e.g. methoxycarbonyl), a $C_{1-6}$ acyl group (e.g. formyl, acetyl), a phenyl group, a tolyl group, (e.g. p- or m-tolyl), a pyridyl group (e.g. 2-pyridyl, 3-pyridyl), a 3-pyridinemethyl group and so on. And the nitrogen-containing heterocyclic group (especially pyridyl, imidazolyl) may form N-oxide.

With respect to the above formula (I), the term "hydroxy-alkyl" represented by $R^5$ stands for an alkyl group having one to six carbon atom(s) substituted by a hydroxy group (e.g. hydroxymethyl) and so on. The "hydroxy-alkyl group" may be substituted with, and is exemplified by a methoxymethyl, acetoxymethyl, ethoxymethyl and carbamoyloxymethyl, as well as a unsubstitutional hydroxymethyl group.

With respect to the above formula (I), the term "esterified carboxyl group" represented by $R^5$ stands for an alkoxy-carbonyl group having 2 to 5 carbon atoms such as a methoxycarbonyl, ethoxycarbonyl, propoxycarbonyl and butoxycarbonyl.

With respect to the above formula (I), the term "amidated carboxyl group" represented by $R^5$ stands for a substitutional aminocarbonyl group whose amino group is substituted with, or a cyclic aminocarbonyl group. Substituents for the amino group of the substitutional aminocarbonyl group include an alkyl group having 1 to 4 carbon atoms (e.g. methyl, ethyl, propyl, butyl), an aryl group having 6 to 10 carbon atoms (e.g. phenyl, naphthyl) (which may have a substituent such as hydroxyl, amino, nitro, halogen, methyl or methoxy at any position on the ring) and a hydroxyl group. The amidated carboxyl group include an aminocarbonyl, a mono- or di-alkylaminocarbonyl having 2 to 4 carbon atoms (e.g., methylaminocarbonyl, ethylaminocarbonyl, isopropylaminocarbonyl, dimethylaminocarbonyl), a phenylaminocarbonyl, a substitutional phenylaminocarbonyl (e.g., p-hydroxyphenylaminocarbonyl, p-methoxyphenylaminocarbonyl, m-chlorophenylaminocarbonyl), a diphenylaminocarbonyl, a hydroxyaminocarbonyl, a N-hydroxy-N-methylaminocarbonyl and a N-hydroxy-N-phenylaminocarbonyl. The cyclic aminocarbonyl include a morpholinocarbonyl and a piperidinocarbonyl.

As $R^5$, hydrogen and methyl are preferable and hydrogen is the most preferable.

The sum of n, an integer from 0 to 12, and m, an integer from 0 to 3, is preferably an integer from 0 to 10, with greatest preference given to 0 as the sum of m and n.

The hydroquinone derivative of the quinone derivative represented by formula (I) is a compound represented by the formula:

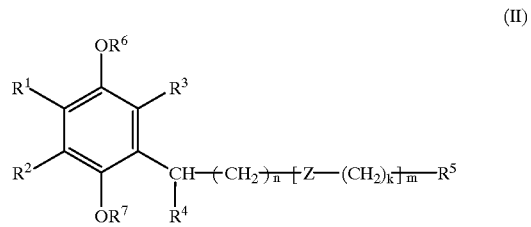

(II)

wherein $R^6$ and $R^7$ independently represent a hydrogen atom or a protective group; and the other symbols are of the same meanings as above formula (I).

The term "protective group" represented by $R^6$ and $R^7$ stands for (i) an acyl group (e.g. acetyl, glucuronyl), (ii) an alkyl group (e.g. methyl, ethyl, isopropyl), (iii) an aralkyl group (e.g. benzyl), (iv) a sulfo group or a salt thereof, (v) a group generally used for a protective group of a phenol or hydroquinone group (e.g. a group described in "Protective group" in organic synthesis, 1991) and so on. Preferable examples of the "protective group" are an acyl group (e.g. acetyl, glucuronyl), a sulfo group or a salt thereof, more preferably an acetyl or a glucuronyl.

The definitions in the formulae (I) and (II) are as follows.

(1) $R^1$ and $R^2$ independently represent a hydrogen atom, an alkyl group, an alkenyl group or an alkoxy group, or may bind together to form —CH=CH—CH=CH—, preferably an alkyl group.

(2) $R^3$ represents a hydrogen atom an alkyl group or an alkenyl group, preferably an alkyl group.

(3) $R^4$ represents an optionally substituted nitrogen-containing heterocyclic group, preferably an optionally substituted pyridyl, imidazolyl or thiazolyl group.

(4) $R^5$ represents a hydrogen atom, an alkyl group, an optionally substituted hydroxy-alkyl group or an optionally esterified or amidated carboxyl group, preferably a hydrogen atom.

(5) Z represents a group represented by:

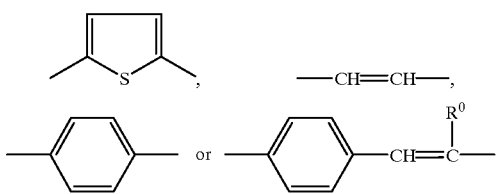

(R⁰ represents a hydrogen atom or an alkyl group).
(6) n represents an integer from 0 to 12, preferably 0.
(7) m represents an integer from 0 to 3, preferably 0.
(8) k represents an integers from 0 to 7.
(9) z and k are arbitrarily variable within the repeat unit in [ ].
(10) $R^6$ and $R^7$ independently represent a hydrogen atom or a protective group, preferably a hydrogen atom or an acyl group, more preferably a hydrogen atom.

Preferable combination of the above symbols are as follows.

(i) n and m is 0; $R^5$ is a hydrogen atom; and the other symbols are of the same meanings as defined above, (ii) n and m is 0; $R^5$ is a hydrogen atom; $R^1$, $R^2$ and $R^3$ independently are an alkyl group or an alkoxy group; and the other symbols are of the same meanings as defined above, (iii) n and m is 0; $R^5$ is a hydrogen atom; $R^1$ is an alkoxy group; $R^2$ and $R^3$ independently are an alkyl group; and the other symbols are of the same meanings as defined above, (iv) n and m is 0; $R^5$ is a hydrogen atom; $R^1$, $R^2$ and $R^3$ independently are an alkyl group; and the other symbols are of the same meanings as defined above, (v) n and m is 0; $R^5$ is a hydrogen atom; $R^1$, $R^2$ and $R^3$ independently are an alkyl group; and $R^4$ is an optionally substituted pyridyl, imidazolyl or thiazolyl group, (vi) n and m is 0; $R^5$ is a hydrogen atom; $R^1$, $R^2$ and $R^3$ are a methyl group; and $R^4$ is an optionally substituted pyridyl, imidazolyl or thiazolyl group, and (vii) n and m is 0; $R^5$ is a hydrogen atom; $R^1$, $R^2$ and $R^3$ are a methyl group; and $R^4$ is 3-pyridyl group.

The following compounds (A), (B), (C), (D), (E), (F) and (G) also have an effect for treating a cachexia in addition to the compounds (I) and (II).

(A) The compound disclosed in EP-0507318-A1:

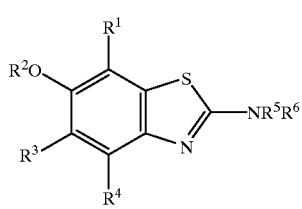

wherein $R^1$ and $R^3$ are either same or different and each represents a hydrogen atom, a lower alkyl group, a lower alkoxy group, a group represented by the formula:

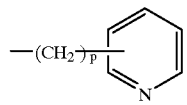

(wherein p is an integer of from 1 to 4), or a group represented by the formula:

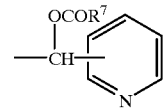

(wherein $R^7$ represents a lower alkyl group);

$R^4$ represents a hydrogen atom, a lower alkyl group, a phenyl group, a group represented by the formula

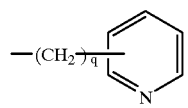

(wherein q is an integer of from 1 to 4), or a group represented by the formula:

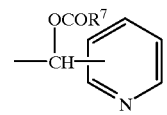

(wherein $R^7$ represents a lower alkyl group);

or $R^3$ and $R^4$ may form a benzene ring together with the carbon atoms to which they are bound;

$R^2$ represents a hydrogen atom or a protective group of a hydroxyl group; and $R^5$ and $R^6$ are either same or different and each represents a hydrogen atom, a lower alkyl group, a group represented by the formula:

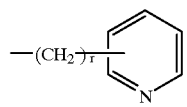

(wherein r is an integer of from 1 to 4), or an acyl group; or a pharmacologically acceptable salt thereof, especially 6-Hydroxy-5,7-dimethyl-2-methylamino-4-(3-pyridylmethyl)benzothiazole.

(B) The compound disclosed in EP-0503426-A1:

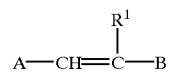

wherein A stands for a group represented by the formula:

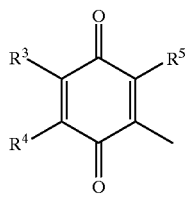

(wherein $R^3$, $R^4$ and $R^5$ is the same or different from each other and each stand for a hydrogen atom, a hydroxyl group, a lower alkyl group, a lower alkoxy group, an alkoxyalkyl group, an alkoxyalkoxy group, a cycloalkylalkoxy group, a thiol group or a thioalkyl group, with the proviso that a case wherein $R^3$ and $R^4$ are each a lower alkoxy group simultaneously is excepted) or a group represented by the formula.

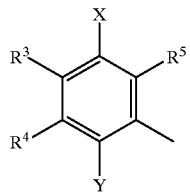

(wherein $R^3$, $R^4$ and $R^5$ is the same or different from each other and each stand for a hydrogen atom, a hydroxyl group, a lower alkyl group, a lower alkoxy group, an alkoxyalkyl group, an alkoxyalkoxy group, a cycloalkylalkoxy group, a thiol group or a thioalkyl group, with the proviso that a case wherein $R^3$ and $R^4$ are each a lower alkoxy group simultaneously is excepted; X and Y is the same or different from each other and each stand for a hydroxyl group or a protected hydroxyl group):

$R^1$ stands for a heteroarylalkyl group; and

B stands for a carboxyl group or a protected carboxyl group, or a pharmacologically acceptable salt thereof, especially (E)-3-(2-Methoxy-3,6-dimethyl-1,4-benzoquinon-5-yl)-2-[5-(3-pyridyl)pentyl]-2-propenoic acid.

(C) The compound disclosed in JP-07-033767:

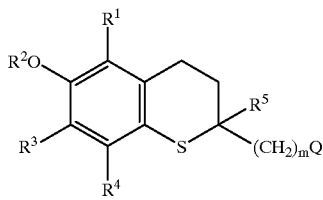

wherein $R^1$ is a hydrogen atom, an optionally substituted alkyl group or an optionally substituted alkenyl group; $R^2$ is a hydrogen atom or a protective group of hydroxy group; $R^3$ and $R^4$ is a hydrogen atom, an optionally substituted alkyl group or an optionally substituted alkenyl group, alkoxyl group or an optionally substituted aryl group, or $R^3$ and $R^4$, taken together, may form —CH═CH—CH═CH—; $R^5$ is an an hydrogen atom or an alkyl group; Q is a nitrogen-containing heterocyclic group; n is 1 to 4, or a pharmacologically acceptable salt thereof.

(D) The compound disclosed in JP-62-223150:

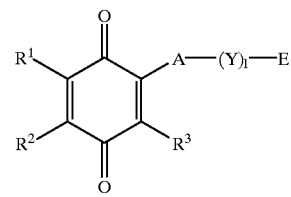

wherein $R^1$ is a lower alkoxy group; $R^2$ is a hydrogen atom or a lower alkoxy group; $R^3$ is a hydrogen atom, lower alkyl group or a lower alkoxy group; A is a lower alkylene group; Y is an oxygen atom,

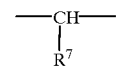

($R^7$ is a hydrogen atom or a lower alkoxy group) or —NH—; E is a phenyl group which may be unsubstituted or substituted by hydroxy, halogen atom or N,N- di lower alkylaminocarbonyl, a naphthyl group which may be unsubstituted or substituted by hydroxy, 1,3-dioxoindanyl or 1,4-naphthoquinoyl or a 5- or 6-membered unsaturated heterocyclic group which may have hydroxy, lower alkyl, lower alkoxy, carboxyl, amino, N,N-di lower alkylaminocarbonyl, hydroxy-lower alkyl, lower alkoxy-carbonyl or oxo, or may be condensed with a benzen ring; ι is 0 or 1, or a salt thereof.

(E) The compound disclosed in EP-0640609-A1:

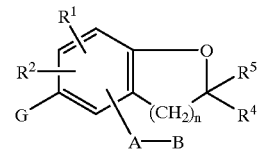

wherein $R^1$ and $R^2$ independently are a hydrogen atom, a halogen atom, a trifluoromethyl group, a cyano group, a $C_{1-10}$ alkyl group, a $C_{1-4}$ alkoxy group, a $C_{3-7}$ cycloalkyl group, a $C_{7-10}$ phenylalkyl group, a $C_{1-10}$ alkyl group substituted by $C_{1-4}$ alkoxy, a $C_{1-4}$ alkyl group substituted by $C_{3-7}$ cycloalkyl, a $C_{1-6}$ alkyl group substituted by phenylthio, a $C_{1-6}$ alkyl substituted by phenoxy, —COOH, —COOR$^6$ (R$^6$ is a $C_{1-6}$ alkyl group), a $C_{2-10}$ alkenyl group, or when they are at ortho-position each other, $R^1$ and $R^2$, taken together, are —CH═CH—CH═CH—;

A is a $C_{1-8}$ alkylene group, a $C_{2-8}$ alkenylene group, a $C_{1-6}$ oxyalkylene group (provided that an oxygen atom is bonded with B) or

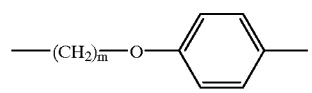

(m is 1–6, provided that B is bonded with phenylene); B is a 5- to 7- membered mono-cyclic hetero ring; G is —OR$^{3A}$ or —NR$^{3B}$R$^{3C}$(R$^{3A}$,R$^{3B}$ and R$^{3C}$ independently are a hydrogen atom, a $C_{1-4}$ alkyl group, a $C_{7-10}$ phenylalkyl group, a $C_{2-5}$ acyl group, a phenylcarbonyl group, a carbonyl group substituted by $C_{7-10}$ phenylalkyl or a $C_{2-4}$ alkoxyalkyl group; $R^4$ and $R^5$ independently are a hydrogen atom, a $C_{1-8}$ alkyl group, a $C_{7-10}$ phenylalkyl group, or $R^4$ and $R^5$, taken together, are a $C_{4-7}$ cycloalkyl group; n is 1 to 3, or a pharmaceutically acceptable salt thereof.

(F) The compound disclosed in JP-05-279340:

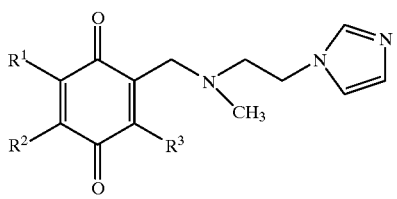

wherein $R^1$, $R^2$ and $R^3$ independently is a hydrogen atom or an optionally substituted lower alkyl, lower alkenyl or aryl group, or a salt thereof.

(G) The compound disclosed in U.S. Pat. No. 5,356,921:

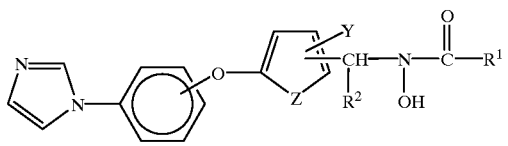

wherein $R^1$ is $NH_2$ or $CH_3$; $R^2$ is H or $CH_3$;
X is O or S; Y is H, OH or $OCH_3$;
Z is —CH═CH—, O or S, or a pharmaceutically acceptable salt thereof.

The above quinone derivative (I) and hydroquinone derivative (II) thereof are easily mutually convertible by chemical or biochemical oxidation and reduction of the quinone and hydroquinone nucleus thereof. Since hydroquinone derivative (II) is usually easily oxidizable by oxygen, air etc., it is normally handled in the form of stable quinone compound (I). Since hydroquinone derivative (II) and quinone compound (I) are easily mutually convertible by chemical or biochemical oxidation and reduction, they can be viewed as equivalent to each other in pharmacological action under physiological conditions.

Structurally, quinone derivative (I) and hydroquinone derivative (II) thereof can have an asymmetric center with respect to the alpha (α) carbon in the side chain of the quinone or hydroquinone nucleus. In such cases optically active compounds exist. Therefore, compounds (I) and (II) include both optical isomers and racemates.

Pharmacologically acceptable salts of the quinone compound represented by general formula (I) and hydroquinone derivative (II) thereof include salts with inorganic acids such as hydrochloric acid, nitric acid, sulfuric acid and phosphoric acid, and salts with organic acids such as methanesulfonic acid, toluenesulfonic acid, benzenesulfonic acid and succinic acid.

Among the compounds of formulas (I) and (II) and pharmaceutically acceptable salts thereof, those wherein $R^4$ is pyridine ring and n is 0 or an integer of 1 to 10 are preferable, those wherein each of m and n is 0 and $R^5$ is hydrogen or methyl are more preferable, and 3,5,6-trimethyl-2-(3-pyridyl)-methyl-1,4-benzoquinone hydrochloride is the most preferable.

Compounds represented by the above formulas (I) and (II) and pharmacologically acceptable salts thereof used for the prophylactic/therapeutic agent in the present invention can be produced by the method described in EP-234729, and so on.

Compounds (I) and (II) and pharmacologically acceptable salts thereof improve a cachexia that is to say a progressive weight loss caused by chronic diseases such as malignant tumors, tuberculosis, diabetes mellitus, hematopathy, endocrinopathy and AIDS, a constitutional syndrome such as anemia, edema, anorexia and malnutrition, and are also low toxicity.

The prophylactic/therapeutic agent of the present invention is used to prevent and treat cachexia in mammals (e.g., mice, rats, rabbits, dogs, monkeys, humans).

The prophylactic/therapeutic agent of the present invention can be safely administered orally or non-orally in the form of compound (I) or (II) or pharmacologically acceptable salt thereof as such, or in a pharmaceutical composition [e.g., tablets, capsules (including soft capsules and microcapsules), liquids, injectable preparations, suppositories] with known pharmaceutically acceptable carriers, excipients and other additives. Dosage varies depending on subject, route of administration, symptoms and other factors. For example, in the case of oral administration to an adult patient with cachexia, compound (I) or (II) or a pharmacologically acceptable salt thereof is normally given at about 0.1 mg/kg to 30 mg/kg body weight, preferably about 2 mg/kg to 20 mg/kg body weight per administration; it is convenient to give this dose 1 to 3 times daily.

The prophylactic/therapeutic agent of the present invention is preferably used against a cachexia resulting from a malignant tumor, particularly its solid cancer. In this case, cachexia can be improved without growthing a malignant tumor.

The present prophylatic and/or therapeutic agent can be also given with the other chemotherapeutic agent and/or immunostimulant agent for the same object at the same time or time intervals.

The chemotherapeutic agents include cancerocidal agents such as alkylating agents (e.g. cyclophosphamide, ifosfamide, etc.), antimetabolic agents (e.g. methotrexate, 5-fluorouracil, etc), antitumor antibiotics (e.g. mitomycin, adriamycin, etc.), plant alkaloids (e.g. vincristine, vindesine, taxol, etc.), cisplatin, carboplatin, etoposide and so on.

The preferable examples of them are 5-fluorouracil derivatives such as furtulon, neofurtulon. And the immunostimulant agents include ingredient of microorganial or bacterial cell wall skeleton (e.g. muramyl dipeptide derivatives, picibanil, etc.), natural immunostimulant polysaccharide (e.g. lentinan, shizophyllan, krestin, etc.), cytokine (e.g. interferon, interleukin, etc.) and colony-stimulating factor (e.g. G-CSF, erythropoietin, etc.) and so on. The preferable examples of them are interleukin such IL-1, IL-2, IL-12.

Further, it also can be used agents such as cyclooxygenase inhibitors (e.g. indomethacin, etc.), progesterone derivatives (e.g. megestrol acetate, etc.), gluco steroids (e.g. dexamethasone, etc.), metoclopramides, tetrahydrocannabinols, eicosapentaenoic acid, growth hormone, ICF-1, antibodies caused by TNF-α, LIF, IL-6 or oncostatin M with the present compounds (I) and (II).

BRIEF DESCRIPTION OF DRAWINGS

FIG. 1 is a graph showing the effect of compound (A) on the body weight of mice bearing MAC16 cancer, obtained in Experimental Example 1.

FIG. 2 is a graph showing the antitumor effect of compound (A) on MAC16, obtained in Experimental Example 1.
Description of the symbols
a=P<0.05 (compared with control by analysis of variance)
b=P<0.01 (compared with control by analysis of variance)

In FIG. 1, the symbols indicate the following:

| | |
|---|---|
| —□— | Control |
| ·····●····· | 5 mg/kg compound (A) |
| —○— | 10 mg/kg compound (A) |
| ----×---- | 25 mg/kg compound (A) |

In FIG. 2, the symbols indicate the following;

| | |
|---|---|
| —□— | Control |
| ·····○····· | 5 mg/kg compound (A) |
| —●— | 10 mg/kg compound (A) |
| ----×---- | 25 mg/kg compound (A) |

BEST MODE FOR CARRYING OUT THE INVENTION

EXAMPLES

The following examples and experimental example are intended to describe this invention in further detail and should by no means be construed as defining the scope of this invention.

Example 1

Capsules

| | | |
|---|---|---|
| (1) | 3,5,6-Trimethyl-2-(3-pyridyl)methyl-1,4-benzoquinone hydrochloride | 100 mg |
| (2) | Fine powder cellulose | 30 mg |
| (3) | Lactose | 37 mg |
| (4) | Magnesium stearate | 3 mg |
| | Total | 170 mg |

The components (1), (2), (3) and (4) were mixed together and packed in a gelatin capsule.

Example 2

Soft capsules

| | | |
|---|---|---|
| (1) | 3,5,6-Trimethyl-2-(3-pyridyl)methyl-1,4-benzoquinone hydrochloride | 50 mg |
| (2) | Corn oil | 100 mg |
| | Total | 150 mg |

The components (1) and (2) were mixed together and packed in a soft capsule in a conventional manner.

Example 3

Tablets

| | | |
|---|---|---|
| (1) | 3,5,6-Trimethyl-2-(3-pyridyl)methyl-1,4-benzoquinone hydrochloride | 100 mg |
| (2) | Lactose | 34 mg |
| (3) | Cornstarch | 10.6 mg |
| (4) | Corn starch (pasty) | 5 mg |
| (5) | Magnesium stearate | 0.4 mg |
| (6) | Carboxymethyl cellulose calcium | 20 mg |
| | Total | 170 mg |

These components were mixed together and tableted using a tableting machine in a conventional manner.

Experimental Example

Therapeutic effect on cachexia in mice with transplanted colon cancer MAC16, and suppressive action against MAC16

A tumor mass of mouse colon cancer MAC16 was frangmentated. Trocar fragments were subcutaneously transplanted to NMRI mice; drug treatment was initiated when the tumor mass reached about 100 mm$^3$ in size at 9 days after transplantation. A solution of 3,5,6-trimethyl-2-(3-pyridyl)methyl-1,4-benzoquinone hydrochloride (hereinafter referred to as compound (A)) in physiological saline was orally administered once a day at doses of 5, 10 and 25 mg/kg. Body weight and tumor size were measured daily; changes in percent ratio to initial values are plotted. In cases where the transplanted tumor ulcerated, the weight loss exceeded 25–30% of control weight loss, the tumor weight reached 10% of the body weight of the cancer-bearing mouse, or the cancer-bearing mouse was dying, the animal was sacrificed in accordance with the British GCCR guidelines for animal welfare. Compound (A) dose-dependently suppressed the progress of body weight loss in the cancer-bearing animal, an index of cachexia in mouse colon cancer MAC16. Since the control mice met the above criteria at 9 days after initial administration, they were sacrificed immediately. In the group receiving compound (A) at 10 or 25 mg/kg, body weight loss was suppressed throughout the experimental period of 17 days following initial administration, without immediate sacrifice, demonstrating a life-prolonging effect.

INDUSTRIAL APPLICABILITY

According to the present invention, cachexia can be improved, especially without making the tumor growth in case that the cachexia is one caused by cancer.

What is claimed is:

1. A method for treating a cancer cachexia in mammals without treating the cancer which comprises administering to a mammal in need of treatment a pharmaceutically effective amount of a quinone derivative of the formula:

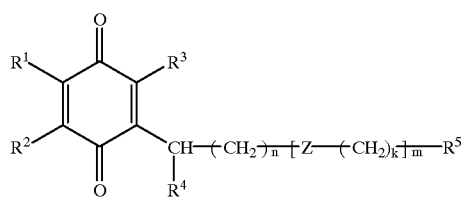

wherein R$^1$ and R$^2$ independently represent a hydrogen atom, an alkyl group, an alkenyl group or an alkoxy group, or may bind together to form —CH=CH—CH=CH—; R$^3$ represents a hydrogen atom, an alkyl group or an alkenyl group; $R^4$ represents an optionally substituted nitrogen-containing heterocyclic group; $R^5$ represents a hydrogen atom, an alkyl group, an optionally substituted hydroxy-alkyl group or an optionally esterified or amidated carboxyl group; Z represents a group represented by:

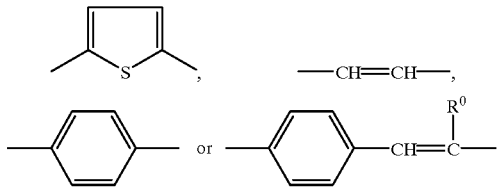

$R^0$ represents a hydrogen atom or an alkyl group; n represents an integer from 0 to 12; m represents an integer from 0 to 3; k represents an integer from 0 to 7; provided that when m is 2 or 3, each Z within the [ ] independently represents a group defined above for Z and each k within the [ ] independently represents an integer from 0 to 7, or a pharmaceutically acceptable salt thereof.

2. The method according to claim 1, wherein $R^1$ and $R^2$ independently are a hydrogen atom, a methyl group or an methoxy group.

3. The method according to claim 1, $R^3$ is a hydrogen atom or a methyl group.

4. The method according to claim 1, wherein the sum of m and n is an integer from 0 to 10.

5. The method according to claim 1, wherein the nitrogen-containing heterocyclic ring group is a 5- or 6- membered heterocyclic group containing at least one nitrogen atom as a ring-forming atom.

6. The method according to claim 1, wherein $R^4$ is a pyridyl group, an imidazolyl group or a thiazolyl group.

7. The method according to claim 1, wherein $R^4$ is a pyridyl group and n is an integer from 0 to 10.

8. The method according to claim 1, wherein m and n are both 0 and $R^5$ is a hydrogen atom or a methyl group.

9. The method according to claim 1, wherein the cancer cachexia originates from a carcinoma.

10. The method according to claim 1, wherein the cancer cachexia originates from a solid cancer.

11. The method according to claim 1, wherein the cancer cachexia originates from a colorectal cancer.

12. The method according to claim 1, wherein $R^1$, $R^2$ and $R^3$ are an alkyl group, n and m are 0, and $R^5$ is a hydrogen atom.

13. The method according to claim 12, wherein $R^4$ is a pyridyl group.

14. A method for treating a cancer cachexia in mammals without treating the cancer which comprises administering to a mammal in need of treatment a pharmaceutically effective amount of 3,5,6-trimethyl-2-(3-pyridyl)methyl-1,4-benzoquinone hydrochloride.

15. A method for treating a cancer cachexia in mammals without treating the cancer, which comprises administering to a mammal in need of treatment a pharmaceutically effective amount of hydroquinone derivative of the formula:

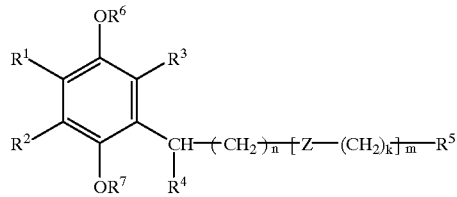

wherein $R^6$ and $R^7$ independently represent a hydrogen atom or a protective group; $R^1$ and $R^2$ independently represent a hydrogen atom, an alkyl group, an alkenyl group or an alkoxy group, or may bind together to form —CH=CH—CH=CH—; $R^3$ represents a hydrogen atom, an alkyl group or an alkenyl group; $R^4$ represents an optionally substituted nitrogen-containing heterocyclic group; $R^5$ represents a hydrogen atom, an alkyl group, an optionally substituted hydroxy-alkyl group or an optionally esterified or amidated carboxyl group; Z represents a group represented by:

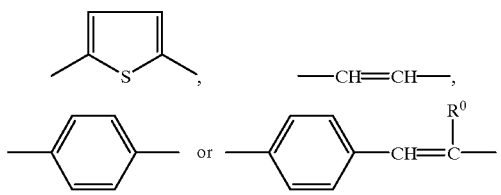

$R^0$ represents a hydrogen atom or an alkyl group; n represents an integer from 0 to 12; m represents an integer from 0 to 3; k represents an integer from 0 to 7; provided that when m is 2 or 3, each Z within the [ ] independently represents a group defined above for Z and each k within the [ ] independently represents an integer from 0 to 7, or a pharmaceutically acceptable salt thereof.

* * * * *